US00PP15131P2

(12) United States Plant Patent
Danziger

(10) Patent No.: US PP15,131 P2
(45) Date of Patent: Aug. 31, 2004

(54) ARGYRANTHEMUM PLANT NAMED 'DANARANBLUSH'

(50) Latin Name: *Argyranthemum frutescens*
Varietal Denomination: Danaranblush

(75) Inventor: Gabriel Danziger, Moshav Nir-Zvi (IL)

(73) Assignee: Danziger Dan Flower Farm (IL)

( * ) Notice: Subject to any disclaimer, the term of this patent is extended or adjusted under 35 U.S.C. 154(b) by 0 days.

(21) Appl. No.: 10/442,892

(22) Filed: May 21, 2003

(51) Int. Cl.[7] ..... A01H 5/00
(52) U.S. Cl. ..... Plt./263

(58) Field of Search ..... Plt./263

*Primary Examiner*—Kent Bell
(74) *Attorney, Agent, or Firm*—Mintz, Levin, Cohn, Ferris, Glovsky and Popeo, P.C.; Ivor R. Elrifi, Esq.; Charles E. Bell, Esq.

(57) ABSTRACT

A new and distinct Argyranthemum plant named 'Danaranblush' characterized by having red ovate ray florets and orange-white colored bell-shaped disc florets when fully opened; bush type vigorous growth with numerous inflorescences per plant; use in the garden as a single plant or planted in groups, as well as use as a border plant and suitable for planting in pots due to its compact growth habit; and growth in full sunlight or partial shade.

2 Drawing Sheets

Latin name of the genus and species of the plant claimed: *Argyranthemum frutescens.*

Variety denomination: 'Danaranblush'; commercially, Argyranthemum cv. 'Angelic Blush'.

BACKGROUND OF THE INVENTION

The present invention relates to a new and distinct cultivar of Argyranthemum plant, botanically known as *Argyranthemum frutescens*, hereinafter referred to by the cultivar name 'Danaranblush'.

The new cultivar originated from a cross made in a controlled breeding program in Moshav Mishmar Hashiva, Israel. The female parent, or seed plant, is identified as number ARF8 (unpatented) of the breeding program. The male parent, or pollen parent, is identified as number ARM10 (unpatented) of the breeding program. 'Danaranblush' was discovered and selected by the inventor, Gabriel Danziger, as a flowering plant within the progeny of the stated cross in a controlled environment in Moshav Mishmar Hashiva, Israel. A descriptive comparison of the new cultivar compared with the parent plants is provided below:

| Characteristic | Danaranblush | ARF8 | ARM10 |
|---|---|---|---|
| Color | white blush | pink | white |
| Flower-shape | anemone | double | single |
| size | 35–40 mm | 35 mm | 40–43 mm |
| flowering time | early | late | early |
| growth habit | compact | compact | compact |

Asexual reproduction of the new cultivar by stem cutting was first performed in January 2000 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danaranblush' which in combination distinguish this Argyranthemum as a new and distinct cultivar:

1. Flower shape and color as illustrated in the photos;
2. Bush type vigourous growth;
3. Early flowering;
4. Use in the garden as a single plant or planted in groups, as well as use as a border plant and for planting in pots; and
5. Growth in full sunlight or partial shade.

'Danaranblush' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Danaranblush' is cultivar 'Blazer Rose' (unpatented).

| Characteristic | 'Danaranblush' | 'Blazer Rose' |
|---|---|---|
| Color | White blush | Pink |
| Flower type | Anemone | Anemone |
| Flower size | 35–40 mm | 30–35 mm |
| Flowering time | early | early |
| Vigor | low | low |
| Growth habit | compact | compact |

BRIEF DESCRIPTION OF THE PHOTOGRAPHS

The accompanying colored photographs illustrate the overall appearance of the new Argyranthemum cultivar showing the colors as true as is reasonably possible with colored reproductions of this type. Plants used in the photographs were about 14 weeks from planting rooted cuttings.

Photograph 1 shows a flowering 'Danaranblush' in its entirety.

Photograph 2 shows a close-up view of a typical inflorescence of 'Danaranblush'.

DETAILED BOTANICAL DESCRIPTION

The following observations, measurements and values describe the new cultivar as grown in Moshav Mishmar Hashiva, Israel under conditions which closely approximate those generally used in commercial practice. The conditions under which the plant was grown include: day time temperature: 16° C.–23° C., night time temperature: 8° C.–12° C., location: open field, light: full sun or semi-shade, irrigation: moist soil, however not surplus, fertilizers: N-200-250 PPM, P-65-75 PPM, K-125-165 PPM. Color references are made to The Royal Horticultural Society Colour Chart (RHS), except where general colors or ordinary significance are used. Color values were taken under daylight conditions at approximately 12:00 pm. in Moshav Mishmar Hashiva, Israel. The age of the plant described is 14 weeks from planting.

Parentage:

*Male parent.*—Proprietary selection of *Argyranthemum frutescens*, identified as number ARM10.

*Female parent.*—Proprietary selection of *Argyranthemum frutescens*, identified as number ARF8.

Classification:

*Botanical.*—*Argyranthemum frutescens.*

*Commercial.*—Argyranthemum 'Danaranblush'.

Propagation: Stem cutting.

Plant description:

*General appearance and form.*—Compact and bushy growth habit; mounded plant form with dense foliage and inflorescences held above the foliage on moderately sized peduncles. Freely and densely branched. Appropriate for containers 10–15 cm in diameter.

*Height.*—25–30 cm.

*Width.*—25 cm.

*Branching.*—Densely branched. Quantity per plant: about 40. Length: 20–30 cm. Diameter: 5–6 mm. Texture: smooth. Internode length: 25–30 mm. RHS color: yellow-green group, 144A.

*Flowering season.*—This variety can flower all year round as long as the temperatures and growing conditions are as specified herein.

*Winter hardiness.*—Hardy in moderate climate.

*Durability to stresses.*—Maintains growth and flowering during moderate winter.

*Lastingness of the individual bloom.*—15–17 days.

*Rooting habit.*—Adventitious roots from cutting base.

*Time to initiate roots.*—10–12 days.

*Time to produce a rooted cutting or liner.*—18–20 days.

*Growth and branching habit.*—Bush type densely branched.

*Crop time.*—12–14 weeks for a flowering pot 10 cm in diameter, ready for sale.

*Fragrance.*—Typical to this species.

Foliage:

*Overall shape of leaf.*—Pinnatipartite.

*Apex.*—Rounded.

*Base.*—Wedge-shaped.

*Length.*—80 mm.

*Width.*—45 mm.

*Margin.*—Parted serrate.

*Texture.*—Slightly warty.

*Color of upper surface.*—Mature leaf: Green group 137-A. Immature leaf: Green group 137-B.

*Color of lower surface.*—Mature leaf: Green group 137-C. Immature leaf: Green group 137-C.

*Venation color.*—Yes. Upper surface: Green group 137-C. Lower surface: Green group 137-D.

*Petiole.*—Length: 22–25 mm. Diameter: 2–3 mm. Color: Yellow green group 146-C.

Inflorescence:

*Quantity of inflorescences.*—Very freely flowering with about 70 flower buds and about 80–100 opened flowers per plant.

*Inflorescence bud.*—Height: 5 mm. Diameter: 5–6 mm. Shape: typical — rounded; observed — rounded. Color: Gray-Brown group 199-B.

*Inflorescence size.*—Diameter: 35–40 mm. Depth (height): 6–7 mm. Diameter of disc: 11–13 mm. Receptacle: depth — 6 mm; diameter — 10 mm.

*Ray florets.*—Shape of outer ray floret: Ovate. Shape of apex: sinuate/tri-dentate. Orientation: horizontal. Length: 17 mm. Width at the center of the floret: 5 mm. Width of apex: 3 mm. Margin: Entire. Texture: Smooth. Number of ray florets per inflorescence: 18–20. Color when opening: Purple 75-D. Color when fully opened upper surface: Red 56-D. Color when fully opened lower surface: Red 49-D.

*Disc florets.*—Shape: Bell-Shaped (campanula). Length: 5–6 mm. Width: 1.5 mm. Apex: Toothed. Margin: Entire. Texture: Smooth. Number of disc florets per inflorescence: 160–180. Color when opening: Gray-orange 174-A. Color when fully opened upper surface: Orange-white 159-C. Color when fully opened lower surface: Orange-white 159-D.

*Stem.*—Average length: 25–30 cm. Average diameter: 5–7 mm. Color: Yellow-green 144-A. Internode length: 25–30 mm.

*Involucral bracts.*—Quantity and arrangement: 15 pcs. Attached to the receptacle bottom. Aspect: Oval. Apex: Rounded (Obtuse). Margin: Entire. Length: 2–3 mm. Width: 1.5 mm. Texture: slightly warty. Upper surface color: Yellow-green 144-C. Lower surface color: Yellow-green 144-B.

*Peduncles.*—Aspect: Upright. Length: 4–5 cm. Diameter: 1.5–2 mm. Texture: Slightly Warty. Color: Yellow-green 146-B.

Reproductive organs:

*Androecium.*—Present on disc florets only.

*Stamen.*—Number: 5 fused as tube. Color: Yellow 13A.

*Seeds.*—Achene. Width: 1 mm. Length: 2 mm. Shape: Achene. Color: Grayed-yellow 161-A.

*Fruit.*—Achene. Color: Grayed-Yellow 161-A.

*Anthers.*—Color: Yellow 13-A.

*Pollen.*—Color: Yellow 13-A.

*Gynoecium.*—Present on ray and disc florets.

*Stigma.*—Color: Yellow 12-B.

*Ovary.*—Color: Yellow-green 149-D.

Disease resistance: Unknown; no susceptibility to pathogens common to Argyranthemum was observed under regular growing conditions.

I claim:

1. A new and distinct Argyranthemum plant named 'Danaranblush', substantially as illustrated and described herein.

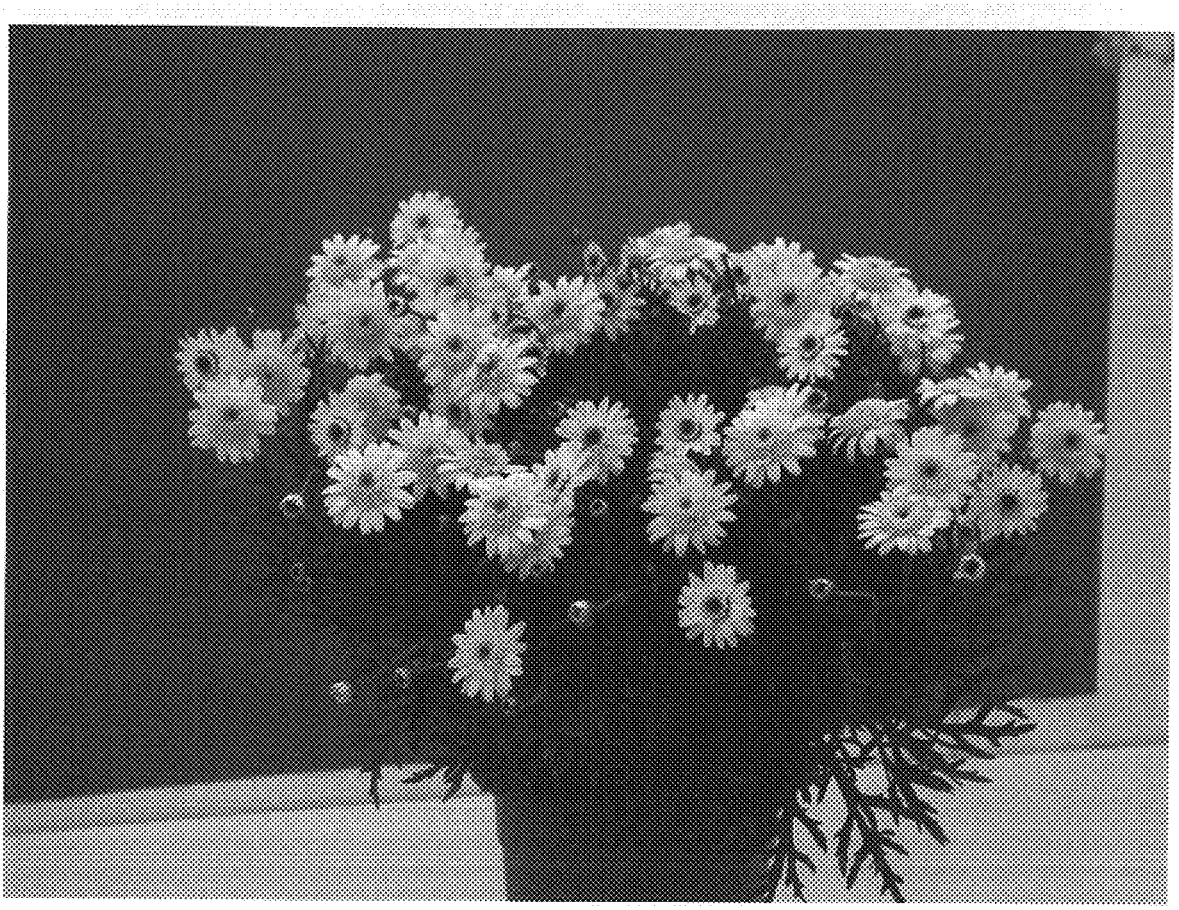

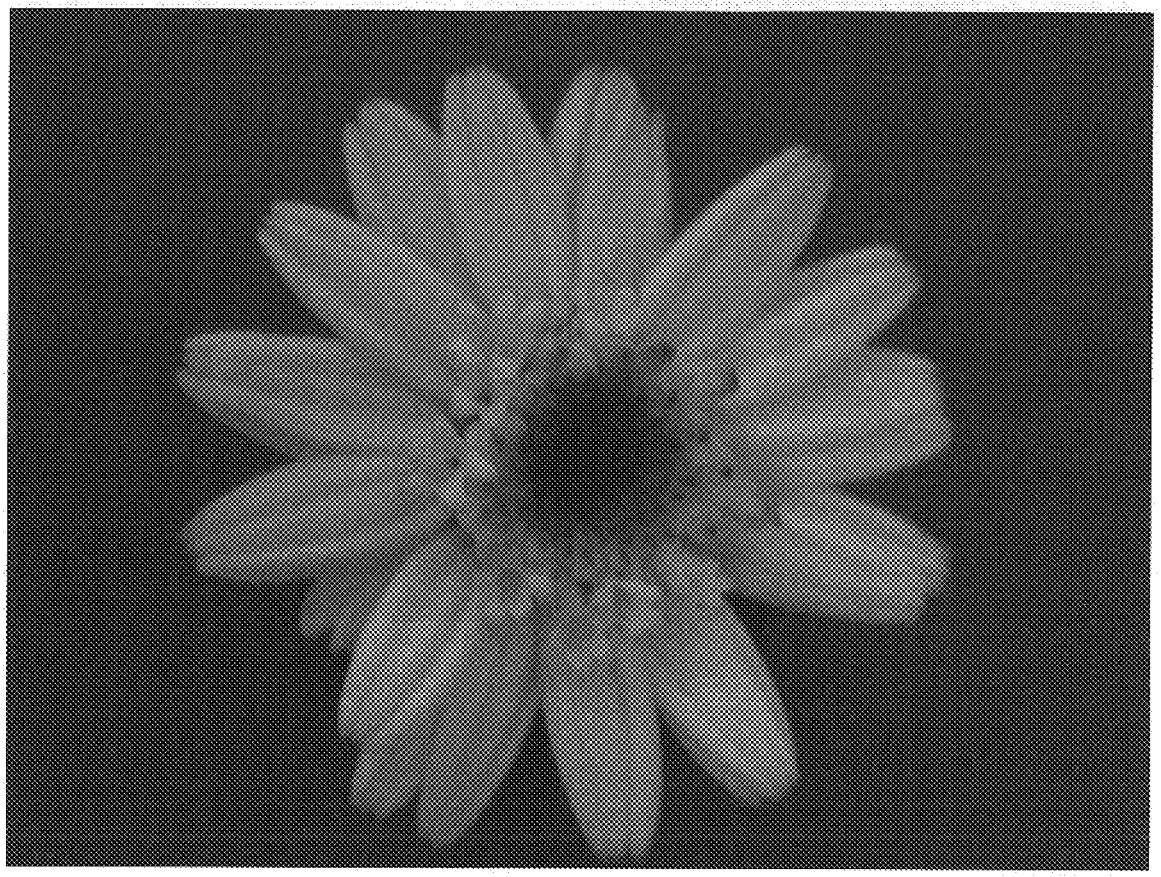

* * * * *